US010495576B2

(12) United States Patent
Matsuo et al.

(10) Patent No.: US 10,495,576 B2
(45) Date of Patent: Dec. 3, 2019

(54) SURFACE-PLASMON ENHANCED FLUORESCENCE MEASUREMENT METHOD, SURFACE-PLASMON ENHANCED FLUORESCENCE MEASUREMENT DEVICE, AND ANALYTICAL CHIP

(71) Applicant: Konica Minolta, Inc., Tokyo (JP)

(72) Inventors: Masataka Matsuo, Tokyo (JP); Hiroshi Hirayama, Tokyo (JP); Yoshimasa Hamano, Tokyo (JP); Tetsuya Noda, Tokyo (JP); Yoshihiro Okumura, Aichi (JP)

(73) Assignee: Konica Minolta, Inc., Tokyo (JP)

( * ) Notice: Subject to any disclaimer, the term of this patent is extended or adjusted under 35 U.S.C. 154(b) by 7 days.

(21) Appl. No.: 15/314,264

(22) PCT Filed: May 29, 2015

(86) PCT No.: PCT/JP2015/065560
§ 371 (c)(1),
(2) Date: Nov. 28, 2016

(87) PCT Pub. No.: WO2015/182747
PCT Pub. Date: Dec. 3, 2015

(65) Prior Publication Data
US 2017/0153182 A1 Jun. 1, 2017

(30) Foreign Application Priority Data
May 29, 2014 (JP) ................. 2014-111298

(51) Int. Cl.
G01N 21/64 (2006.01)
(52) U.S. Cl.
CPC .................. *G01N 21/648* (2013.01)
(58) Field of Classification Search
None
See application file for complete search history.

(56) References Cited

U.S. PATENT DOCUMENTS 8,026,494 B2 * 9/2011 Kimura ................ G01N 21/648
250/458.1
2006/0141611 A1 * 6/2006 Frutos .................. G01N 21/253
435/287.2
(Continued)

FOREIGN PATENT DOCUMENTS

EP 2228637 A1 9/2010
EP 2711689 A1 3/2014
(Continued)

OTHER PUBLICATIONS

European Patent Application No. 15799969.9; Extend Search Report; dated Nov. 7, 2017; 11 pages.
(Continued)

*Primary Examiner* — Edwin C Gunberg
(74) *Attorney, Agent, or Firm* — Baker Hostetler

(57) ABSTRACT

First, an analytical chip having a prism, a metal film that includes a trapping region having immobilized on the surface thereof a trapping element for trapping a substance to be analyzed, and a mark in which the scatter of emitted plasmon scattered light differs from the scatter of plasmon scattered light emitted from the surrounding region, is disposed in a chip holder. Next, the rear surface of the metal film is irradiated with excitation light, plasmon scattered light emitted from the proximity of the mark is detected, and, on the basis of the detected plasmon scattered light, location information for the trap region is obtained. Next, the portion of the rear surface of the metal film that corresponds to the trap region arranged at the detected location is irradiated with excitation light, and fluorescence emitted by a fluorescent substance is detected.

17 Claims, 5 Drawing Sheets

(56) References Cited

U.S. PATENT DOCUMENTS

2011/0240879 A1   10/2011  Shiraishi et al.
2012/0126142 A1    5/2012  Matsui et al.
2015/0011015 A1    1/2015  Matsuo et al.

FOREIGN PATENT DOCUMENTS

| | | |
|---|---|---|
| JP | 2007-093250 A | 4/2007 |
| JP | 2008-267959 A | 11/2008 |
| JP | 2010-286421 A | 12/2010 |
| JP | 2012-117931 A | 6/2012 |
| WO | WO 2012/093437 A1 | 7/2012 |
| WO | 2013/099871 A1 | 4/2013 |
| WO | WO 2014/076926 A1 | 5/2014 |

OTHER PUBLICATIONS

International Search Report, from PCT/JP2015/065560 with an international filing date of May 29, 2015, dated Sep. 1, 2015, 4 pgs., Japanese Patent Office, Tokyo, Japan.

English Translation of the International Prelimary Report on Patentability, from PCT/JP2015/065560 with an international filing date of May 29, 2015, dated Dec. 8, 2016, 8 pgs., International Bureau of WIPO, Geneva, Switzerland.

Japan Patent Application No. 2016-523576; Notice of Reasons for Rejection; dated Jul. 3, 2018; 8 pages.

European Patent Application No. 15799969.9; Office Action—Article 94(3); dated Jun. 5, 2019; 9 pages.

\* cited by examiner

SURFACE-PLASMON ENHANCED FLUORESCENCE MEASUREMENT METHOD, SURFACE-PLASMON ENHANCED FLUORESCENCE MEASUREMENT DEVICE, AND ANALYTICAL CHIP

CROSS-REFERENCE TO RELATED APPLICATIONS

This application is a U.S. National Stage filing, under 35 U.S.C. 371, of International Application No. PCT/JP2015/065560, filed May 29, 2015, which claims the benefit of Japanese application number 2014-111298, filed May 29, 2014, the disclosures of which, including the specification, drawings, and abstract, are incorporated herein by reference in their entirety.

BACKGROUND OF THE INVENTION

Technical Field

The present invention relates to a surface-plasmon enhanced fluorescence measurement method and a surface-plasmon enhanced fluorescence measurement device for detecting a detection-target substance contained in a sample solution, using surface plasmon resonance (SPR), and also relates to an analysis chip used in detection of the detection-target substance contained in the sample solution.

Background Art

Highly-sensitive and quantitative detection of a slight amount of a detection-target substance in measurement for detecting biological substances such as protein and DNA makes it possible to immediately figure out the condition of a patient and treat the patient. For this reason, there has been a demand for an analysis method and an analysis device for highly-sensitive and quantitative detection of weak light caused by a slight amount of the detection-target substance. As an exemplary method of detecting a detection-target substance with high sensitivity, a surface plasmon resonance fluorescence analysis (Surface Plasmon-field enhanced Fluorescence Spectroscopy (SPFS)) is known.

SPFS uses a prism provided with a metal film disposed on a predetermined surface of the prism. Irradiation of the metal film with excitation light through the prism at an angle at which surface plasmon resonance occurs can generate localized light (enhanced electric field) on the surface of the metal film. This localized light excites a fluorescent substance used for labeling the detection-target substance captured on the metal film, therefore making it possible to detect the presence or amount of the detection-target substance through detection of the fluorescence emitted from the fluorescent substance.

In SPFS, highly-sensitive and accurate detection requires accurate positioning of the analysis chip. Accurate detection of the amount (density) of the detection-target substance requires accurate adjustment of the incident angle of excitation light. However, when the analysis chip is shifted in position, accurate adjustment of the incident angle of the excitation light is impossible. In addition, the irradiation spot of the excitation light and the reaction site on the metal film preferably coincide with each other in shape and position for highly-sensitive detection of the detection-target substance. However, when the analysis chip is shifted in position, the irradiation spot of excitation light cannot be adjusted accurately in shape and position. Meanwhile, requiring users to accurately position the analysis chip is unfavorable in terms of usability.

There have been proposed methods for positioning an analysis chip in methods for detecting a detection-target substance by irradiating the analysis chip with light although they are not SPFS. For example, Patent Literature (hereinafter, referred to as "PTL") 1 discloses identifying the position of an analysis chip (biochip) through irradiation of the analysis chip with illumination light different from excitation light in wavelength and detection of reflection light or transmission light of the illumination light in detection using a fluorescent substance. The use of illumination light different from excitation light in wavelength makes it possible to identify the position of the analysis chip while preventing the fluorescent substance from being discolored.

CITATION LIST

Patent Literatures

PTL 1
Japanese Patent Application Laid-Open No. 2007-093250

SUMMARY OF THE INVENTION

Technical Problem

The positioning method disclosed in PTL 1 has a problem that the manufacturing costs of analysis chips increase because the method requires addition of a light source different from the excitation light source, and a wavelength limiting filter, for example.

An object of the present invention is to provide a surface-plasmon enhanced fluorescence measurement method, a surface-plasmon enhanced fluorescence measurement device, and an analysis chip each enabling accurate positioning of the analysis chip while preventing an increase in manufacturing costs of the analysis chip and surface-plasmon enhanced fluorescence measurement device.

Solution to Problem

To solve the above-mentioned problems, a surface-plasmon enhanced fluorescence measurement method according to an embodiment of the present invention is a method in which fluorescence that is emitted from a fluorescent substance for labeling a detection-target substance when the fluorescent substance is excited by localized light based on surface plasmon resonance is detected to detect the presence or amount of the detection-target substance, the method including: installing an analysis chip to a chip holder fixed to a conveyance stage, the analysis chip including: a prism having an incidence surface, an emission surface, and a film-formation surface; a metal film disposed on the film-formation surface and including a capturing region having a surface to which a capturing body for capturing the detection-target substance is fixed; and one or more marks each of which is formed on a plane identical to that of the metal film and in which a scattered state of plasmon scattering light emitted from the mark is different from a scattered state of plasmon scattering light emitted from a region around the mark; irradiating a rear surface of the metal film corresponding to the mark in the analysis chip installed to the chip holder with excitation light through the incidence surface, detecting plasmon scattering light emitted from the vicinity of the mark, and obtaining position information of the capturing region based on the detected plasmon scattering light; moving the chip holder by the conveyance stage based on the position information to move the captured region to a detection position; and irradiating a rear surface of the metal film corresponding to the capturing region disposed at the detection position with excitation light and detecting fluorescence emitted from the fluorescent substance for labeling the detection-target substance captured by the capturing body.

To solve the above-mentioned problems, a surface-plasmon enhanced fluorescence measurement device according to an embodiment of the present invention is a device configured to detect fluorescence that is emitted from a fluorescent substance for labeling a detection-target substance when the fluorescent substance is excited by localized light based on surface plasmon resonance and to detect the presence or amount of the detection-target substance, the device including: a chip holder configured to detachably hold an analysis chip including: a prism having an incidence surface, an emission surface, and a film-formation surface; a metal film disposed on the film-formation surface and including a capturing region having a surface to which a capturing body for capturing the detection-target substance is fixed; and a mark in which a scattered state of plasmon scattering light emitted from the mark is different from a scattered state of plasmon scattering light emitted from a region around the mark; a conveyance stage configured to move the chip holder; an excitation-light irradiating section configured to irradiate a rear surface of the metal film with excitation light through the incidence surface; a plasmon-scattering-light detecting section configured to detect plasmon scattering light emitted from the metal film; a position adjustment section configured to identify a position of the capturing region of the analysis chip held by the chip holder, based on a detection result of the plasmon-scattering-light detecting section on plasmon scattering light based on the excitation light with which a rear surface of the metal film corresponding to the mark is irradiated, and to move the chip holder via the conveyance stage to move the capturing region of the analysis chip to a detection position; and a fluorescence detection section configured to detect fluorescence emitted from a fluorescent substance for labeling the detection-target substance captured by the capturing body.

An analysis chip according to an embodiment of the present invention is a chip configured to be used for detecting fluorescence that is emitted from a fluorescent substance for labeling a detection-target substance when the fluorescent substance is excited by localized light based on surface plasmon resonance and to be used for detecting the presence or amount of the detection-target substance, the chip including: a prism including: an incidence surface, an emission surface, and a film-formation surface; a metal film disposed on the film-formation surface of the prism and including a capturing region having a surface to which a capturing body for capturing the detection-target substance is fixed; and a positioning mark in which a scattered state of plasmon scattering light emitted from the positioning mark is different from a scattered state of plasmon scattering light emitted from a region around the positioning mark.

Advantageous Effects of Invention

According to the present invention, accurate positioning of an analysis chip can be realized. Thus, according to the present invention, highly-sensitive and accurate detection of a detection-target substance is made possible while an increase in manufacturing costs is prevented.

DESCRIPTION OF EMBODIMENTS

Hereinafter, an embodiment of the present invention will be described in detail with reference to the accompanying drawings.

Figure 1:
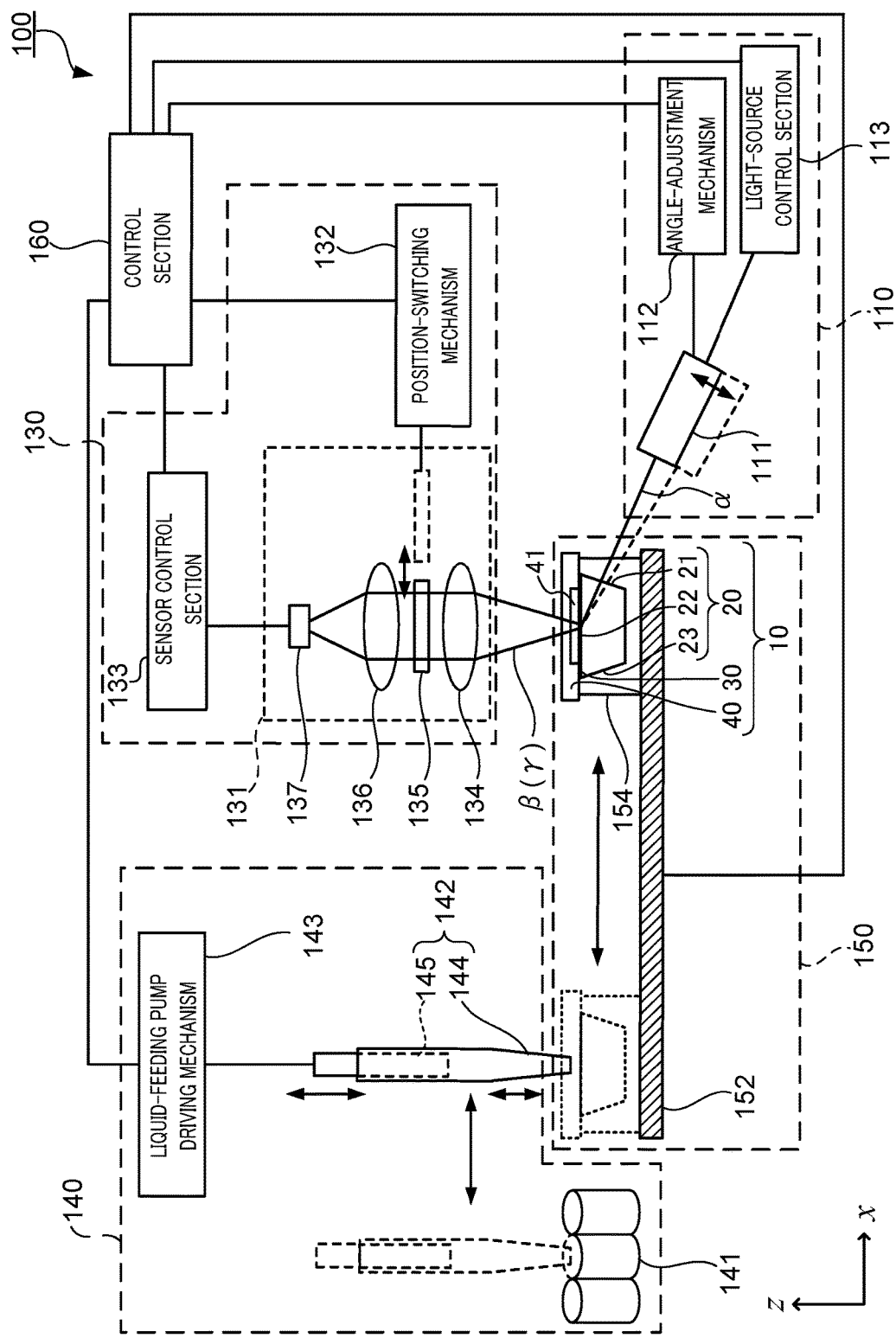
FIG. 1 is a diagram schematically illustrating a configuration of an SPFS device according to Embodiment 1 of the present invention.
Figure 2:
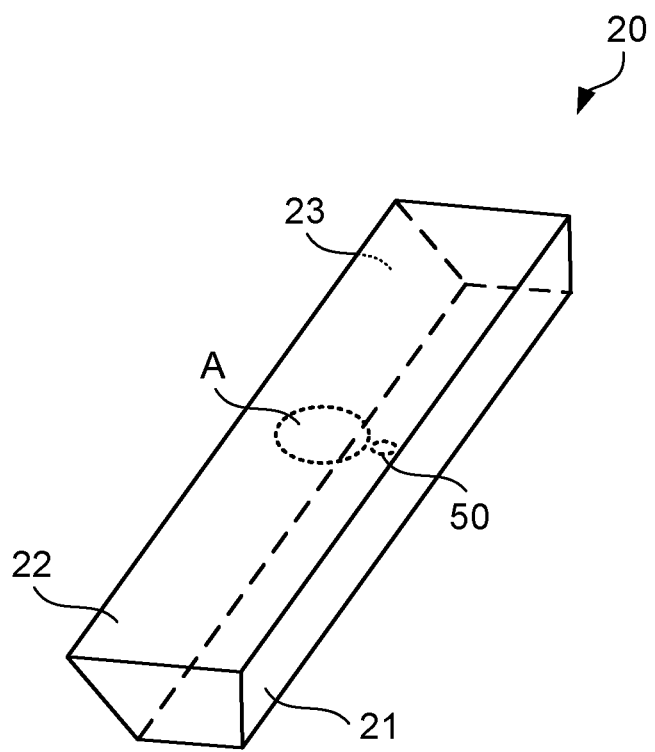
FIG. 2 is a diagram illustrating a positional relationship between a capturing region and a mark.

FIG. 1 is a schematic view illustrating a configuration of surface-plasmon enhanced fluorescence measurement device (SPFS device) 100 according to an embodiment of the present invention. FIG. 2 is a diagram illustrating a positional relationship between a capturing region and a mark.

As illustrated in FIG. 1, SPFS device 100 includes excitation-light irradiation unit 110, response-light detection unit 130, liquid-feeding unit 140, conveyance unit 150, and control section 160. SPFS device 100 is used in a state where analysis chip 10 is attached to chip holder 154 of conveyance unit 150. Thus, a description will be given of analysis chip 10, first, followed by a description of each component of SPFS device 100.

[Configuration of Analysis Chip]

Analysis chip 10 includes: prism 20 including incidence surface 21, film-formation surface 22, and emission surface 23; metal film 30 formed on film-formation surface 22; mark 50 disposed on film-formation surface 22 or metal film 30; and channel closure 40 disposed on film-formation surface 22 or metal film 30. Usually, analysis chip 10 is replaced for each analysis.

Prism 20 is composed of a dielectric which is transparent to excitation light α. Prism 20 includes incidence surface 21, film-formation surface 22, and emission surface 23. Incidence surface 21 is a surface through which excitation light α from excitation-light irradiation unit 110 enters prism 20. Metal film 30 is disposed on film-formation surface 22. Excitation light α having entered prism 20 is reflected by the rear surface of metal film 30. More specifically, excitation light α is reflected by an interface (film-formation surface 22) between prism 20 and metal film 30. Emission surface 23 is a surface through which excitation light α reflected by the rear surface of metal film 30 is emitted out of prism 20.

Prism 20 is not limited to any particular shape. In this embodiment, prism 20 is in a columnar shape having a trapezoid as its bottom surface. The surface of the columnar shape corresponding to one bottom side of the trapezoid is film-formation surface 22 while the surface thereof corresponding to one leg of the trapezoid is incidence surface 21, and the surface thereof corresponding to the other leg of the trapezoid is emission surface 23. Preferably, the trapezoid serving as the bottom surface is an isosceles trapezoid. This configuration makes incidence surface 21 and emission surface 23 symmetric and makes it harder for an S-wave component of excitation light α to stay in prism 20.

Incidence surface 21 is formed such that excitation light α does not return to excitation-light irradiation unit 110. When the light source of excitation light α is a laser diode (hereinafter, may be referred to as "LD"), returning excitation light α to the LD disturbs the excitation state of LD, causing the wavelength and the output of excitation light α to vary. Thus, the angle of incidence surface 21 is set within a scanning range around an ideal enhanced angle to prevent excitation light α from perpendicularly entering incidence surface 21. In this embodiment, the angle between incidence surface 21 and film-formation surface 22 and the angle between film-formation surface 22 and emission surface 23 are each approximately 80 degrees.

Note that, the design of analysis chip 10 substantially determines the resonance angle (and the enhanced angle in the close vicinity thereof). The design factors include the refractive index of prism 20, the refractive index of metal film 30, the film thickness of metal film 30, the extinction coefficient of metal film 30, the wavelength of excitation light α, the refractive index of a measurement solution introduced into a channel during measurement, and the like. While the resonance angle and the enhanced angle shift due to the detection-target substance fixed to metal film 30, the amount of shift in this case is less than several degrees.

Prism 20 has a birefringence property to a certain degree. Examples of the material of prism 20 include a resin and glass. Preferably, the material of prism 20 is a resin having a refractive index of 1.4 to 1.6 and causing a small birefringence.

Metal film 30 is disposed on film-formation surface 22 of prism 20. Thus, interaction (surface plasmon resonance) occurs between photons of excitation light α incident on film-formation surface 22 under the total reflection condition and free electrons in metal film 30, thus making it possible to generate localized light on the surface of metal film 30.

The material of metal film 30 is not limited to any particular one as long as a metal capable of causing surface plasmon resonance is employed. Examples of the material of metal film 30 include gold, silver, copper, aluminum, and their alloys. In this embodiment, metal film 30 is a gold thin film. The method of forming metal film 30 is not limited to any particular one. Examples of the method of forming metal film 30 include sputtering, vapor deposition, and plating. The thickness of metal film 30 is not limited to any particular thickness, but preferably is in a range from 30 to 70 nm.

Capturing region A is disposed on at least a part of the surface of metal film 30 not facing prism 20 (top surface of metal film 30). A capturing body for capturing the detection-target substance is fixed to capturing region A. Fixing the capturing body to the region enables selectively detecting the detection-target substance. The planar view shape of capturing region A is not limited to any particular shape. Examples of the planar view shape of capturing region A include a circle and a polygon. Note that, in this embodiment, the planar view shape of capturing region A is a circle. The type of capturing body is not limited to a particular one as long as it is capable of capturing the detection-target substance. In this embodiment, the capturing body is an antibody specific to the detection-target substance or a fragment of the antibody.

As illustrated in FIG. 2, mark 50 is disposed on film-formation surface 22 of prism 20, or metal film 30. Mark 50 serves as a reference for positioning capturing region A. Although a detailed description will be given hereinafter, the positioning of capturing region A is performed based on a scattered state of plasmon scattering light emitted from the vicinity of mark 50 and the surrounding region thereof. For this reason, as long as mark 50 is formed to cause the scattered state of plasmon scattering light emitted therefrom to be different from the scattered state of plasmon scattering light emitted from a region other than mark 50, mark 50 is not limited to any particular one. Examples of mark 50 include a protrusion or a recess formed in film-formation surface 22, an exposed shaped film, a patterned metal film, and a seal attached to metal film 30.

As described above, irradiation with excitation light α while metal film 30 is disposed on film-formation surface 22 generates plasmon scattering light γ. Thus, the intensity of plasmon scattering light γ generated at mark 50 decreases when mark 50 is exposed film-formation surface 22 or patterned metal film 30, so that the position where the intensity of plasmon scattering light γ generated at mark 50 has decreased is detectable as mark 50.

Plasmon scattering light γ is generated when excitation light α enters metal film 30 on film-formation surface 22, and the intensity of plasmon scattering light γ depends on the incident angle of excitation light α. As will be described hereinafter, in order to detect fluorescence β of high intensity, fluorescence β is measured at an angle where the largest light amount of plasmon scattering light γ can be obtained or at an angle close to this angle in actual measurement. When mark 50 is a protrusion or a recess formed in film-formation surface 22, there exists a surface at an angle different from the angle of film-formation surface 22 and metal film 30 in analysis chip 10. Since the intensity of plasmon scattering light γ depends on the incident angle of excitation light α, the position where the intensity of plasmon scattering light γ changes can be detected as mark 50.

Moreover, when a seal having a light blocking property is used as mark 50, since plasmon scattering light γ generated from mark 50 decreases, the position where the intensity of plasmon scattering light γ decreases can be detected as mark 50. Meanwhile, when a seal having no light blocking property is used as mark 50, use of a material having a refractive index different from the refractive index of the liquid in channel 41 as the material of the seal makes it possible to detect the position where the intensity of plasmon scattering light γ changes, as mark 50. The intensity of plasmon scattering light γ changes depending on the refractive index of prism 20, the refractive index of metal film 30, the film thickness of metal film 30, the extinction coefficient of metal film 30, the wavelength of excitation light α, the refractive index of the measurement liquid introduced into the channel during measurement, and/or the like. Stated differently, since the intensity of plasmon scattering light γ differs depending on whether or not a seal is present on metal film 30, or whether or not a measurement solution is present, the position where the intensity of plasmon scattering light γ changes can be detected as mark 50. As described above, the use of plasmon scattering light γ to be detected makes it possible to detect the position of mark 50.

Mark 50 is preferably formed in a structure opposite to the traveling direction of excitation light α when metal film 30 is viewed in its normal direction. This is because irradiation of the portion of the opposite structure with excitation light α cause the scattered state of plasmon scattering light γ to change more significantly, thus making it possible to increase the detection accuracy for the position of mark 50. The effect of forming this structure opposite to excitation light α is more effective than that of the protrusion or recess or the patterning shape of metal film 30 described above.

Moreover, the position where mark 50 is formed is not limited to any particular position. Mark 50 may be disposed inside or outside of capturing region A when metal film 30 is viewed from its normal direction. In this embodiment, mark 50 is disposed at a position outside of capturing region A. Moreover, the position where mark 50 is formed may overlap with the light path of excitation light α or may be outside of the light path of excitation light α when metal film 30 is viewed from its normal direction. When mark 50 is disposed inside of capturing region A in particular, the positioning to be described hereinafter can be more surely performed because a distance between mark 50 and the measurement region during measurement is small. Meanwhile, disposing mark 50 outside of capturing region A is also preferable because mark 50 does not hinder detection of fluorescence when fluorescence β is detected from a fluorescent substance through irradiation with excitation light α within capturing region A after the positioning to be described, hereinafter. Furthermore, mark 50 may be disposed in a conveyance direction in which analysis chip 10 is conveyed with respect to capturing region A when metal film 30 is viewed from its normal direction. As a result, both mark 50 and capturing region A can be irradiated with excitation light α, using conveyance unit 150 of analysis chip 10.

Moreover, the number of marks 50 is not limited in particular. The number of marks 50 may be one or more. In this embodiment, the number of marks 50 is one. The area of mark 50 when metal film 30 is viewed from its normal direction is not limited in particular either. In this embodiment, the area of mark 50 is preferably of a size that fits into the irradiation spot of irradiation light when metal film 30 is viewed from its normal direction. When the area of mark 50 in planar view is larger than the area of the irradiation spot of irradiation light in planar view, it may become difficult to accurately identify the position of mark 50.

Moreover, when two or more marks 50 are disposed, marks 50 are formed in a direction orthogonal to the conveyance direction of analysis chip 10, for example. In this case, disposing analysis chip 10 or excitation-light irradiation unit 110 or a drive mechanism in which excitation-light irradiation unit 110 and response light detection unit 130 are integrally driven (not illustrated) makes it possible to perform positioning in two directions (irradiation direction of excitation light α and its orthogonal direction), using two marks 50. In another case where two or more marks 50 are disposed, two marks 50 are formed at positions opposite to each other with respect to capturing region A when metal film 30 is viewed in its normal direction, for example. Detecting the positions of two marks 50 makes it possible to figure out that capturing region A is positioned at a middle point between the two positions, so that, even when the detection accuracy for one of marks 50 is low, the position of capturing region A can be accurately detected.

Channel closure 40 is disposed on metal film 30. When metal film 30 is formed on only a part of film-formation surface 22 of prism 20, channel closure 40 may be disposed on film-formation surface 22. A channel groove is formed in the rear surface of channel closure 40, and channel closure 40 forms channel 41 together with metal film 30 (and prism 20) through which liquid flows. Examples of the liquid include a sample solution containing the detection-target substance, a labeling solution containing an antibody labeled by a fluorescent substance, a washing solution and the like. Capturing body A of metal film 30 is exposed inside of channel 41. Both ends of channel 41 are respectively connected to an inlet and outlet (not illustrated) formed in the top surface of channel closure 40. When liquid is injected into channel 41, the liquid makes contact with the capturing body of capturing region A.

Channel closure 40 is preferably composed of a material transparent to fluorescence β and plasmon scattering light γ emitted from metal film 30. Examples of the material of channel closure 40 include a resin. As long as the part of channel closure 40 used for taking out fluorescence β and plasmon scattering light γ to the outside is transparent to fluorescence β and plasmon scattering light γ, another part of channel closure 40 may be formed of an opaque material. Channel closure 40 is bonded to metal film 30 or prism 20 by adhesion using a double-sided tape, an adhesive and/or the like, laser welding, ultrasound welding, or pressure bonding using a clamp member and/or the like, for example.

As illustrated in FIG. 1, excitation light α enters prism 20 from incidence surface 21. Excitation light α having entered prism 20 is incident on metal film 30 at a total reflection angle (angle at which surface plasmon resonance occurs). Metal film 30 is thus irradiated with excitation light α at an angle which surface plasmon resonance occurs, and thus, localized light (which is also generally called "evanescent light" or "near-field light") can be generated on metal film 30. This localized light excites the fluorescent substance labeling the detection-target substance existing on metal film 30, and fluorescence β is emitted. SPFS device 100 can detect the presence or amount of the detection-target substance through detection of the light amount of fluorescence β emitted from the fluorescent substance.

[Configuration of SPFS Device]

Next, the configuration elements of SPFS device 100 will be described. As described above, SPFS device 100 includes excitation-light irradiation unit 110, response-light detection unit 130, liquid-feeding unit 140, conveyance unit 150 and control section 160.

Excitation-light irradiation unit 110 emits excitation light α to analysis chip 10 (rear surface of metal film 30) held by chip holder 154. During measurement of fluorescence β, excitation-light irradiation unit 110 emits only P-wave with respect to metal film 30 toward incidence surface 21 such that the incident angle with respect to metal film 30 is an angle at which surface plasmon resonance occurs. The term "excitation light" used herein is light which directly or indirectly excites a fluorescent substance. For example, excitation light α is light generating localized light which excites a fluorescent substance on the surface of metal film 30 when excitation light α is emitted to metal film 30 through prism 20 at an angle at which surface plasmon resonance occurs. In SPFS device 100 according to this embodiment, excitation light α is used also for positioning of analysis chip 10.

Excitation-light irradiation unit 110 includes a configuration for emitting excitation light α toward prism 20, and a configuration for changing the incident angle of excitation light α with respect to the rear surface of metal film 30. In this embodiment, excitation-light irradiation unit 110 includes light source unit 111, angle-adjustment mechanism 112 and light-source control section 113.

Light source unit 111 emits collimated excitation light α having a constant wavelength and a constant light amount such that the irradiation spot on the rear surface of metal film 30 has a substantially circular shape. Light source unit 111 includes, for example, a light source of excitation light α, a beam-shaping optical system, an APC mechanism and a temperature adjustment mechanism (which are not illustrated).

The light source is not limited to any particular type, and is a laser diode (LD), for example. Other examples of the light source include a light-emitting diode, a mercury lamp, and other laser light sources. When the light emitted from the light source is not a beam, the light emitted from the light source is converted into a beam by a lens, a mirror, a slit and/or the like. In addition, when the light emitted from the light source is not monochromatic light, the light emitted from the light source is converted into monochromatic light by a diffraction grid or the like. Furthermore, when the light emitted from the light source is not linear polarization, the light emitted from the light source is converted into light of linear polarization by a polarizer and/or the like.

The beam-shaping optical system includes a collimator, a bandpass filter, a linear polarization filter, a half-wave plate, a slit, a zooming unit and the like, for example. The beam-shaping optical system may include some or all of these components. The collimator collimates excitation light α emitted from the light source. The bandpass filter changes excitation light α emitted from the light source into narrow-band light composed only of a central wavelength. This is because excitation light α from the light source has a slight wavelength distribution width. The linear polarization filter changes excitation light α emitted from the light source into complete linearly polarized light. The half-wave plate adjusts the polarization direction of excitation light α such that the P-wave component is incident on metal film 30. The slit and the zooming unit adjust the beam diameter, the outline shape and/or the like of excitation light α such that the shape of the irradiation spot on the rear surface of metal film 30 has a circular shape having a predetermined size.

The APC mechanism controls the light source so as to keep the output of the light source constant. More specifically, the APC mechanism detects the light amount of the light diverged from excitation light α by a photodiode (not illustrated) or the like. The APC mechanism then controls the input energy by a recurrent circuit to control the output of the light source to remain constant.

The temperature adjustment mechanism is composed of a heater, a Peltier device, or the like, for example. The wavelength and energy of the light emitted from the light source may vary depending on the temperature. Therefore, keeping the temperature of the light source constant using the temperature adjustment mechanism controls the wavelength and energy of the light emitted from the light source to remain constant.

Angle-adjustment mechanism 112 adjusts the incident angle of excitation light α to the rear surface of metal film 30 (the interface (film-formation surface 22) between prism 20 and metal film 30). Angle-adjustment mechanism 112 relatively turns the optical axis of excitation light α and chip holder 154 to emit excitation light α toward a predetermined position of the rear surface of metal film 30 at a predetermined incident angle through prism 20.

For example, angle-adjustment mechanism 112 turns light source unit 111 around an axis orthogonal to the optical axis of excitation light α (axis perpendicular to the sheet surface of FIG. 1). At this time, the position of the turning axis is set such that the position of the irradiation spot on metal film 30 barely changes even when the incident angle is changed. Setting the position of the turning center at a position near the intersection of the optical axes of two rays of excitation light α at both ends of the scanning range of the incident angle (position between the irradiation position on film-formation surface 22 and incidence surface 21) makes it possible to minimize shifting of the irradiation position.

In the incident angle of excitation light α with respect to the rear surface of metal film 30, the angle at which the largest light amount of plasmon scattering light γ is obtainable is the enhanced angle. Setting the incident angle of excitation light α to the enhanced angle or an angle close to the enhanced angle enables measurement of fluorescence β of high intensity. While the material and the shape of prism 20 of analysis chip 10, the film thickness of metal film 30, the refractive index of the liquid in channel 41 and the like determine the basic incident condition of excitation light α, the optimum incident condition slightly varies depending on the type and amount of detection-target object captured in channel 41, non-specific adsorption of a foreign substance in the sample, shaping errors of prism 20 and the like. Therefore, the optimum enhanced angle is preferably determined for each measurement. In this embodiment, the favorable emission angle of excitation light α with respect to the normal of metal film 30 (straight line along the z-axis direction in FIG. 1) is approximately 70 degrees.

Light-source control section 113 controls various components included in light source unit 111 to control emission of emission light (excitation light α) of light source unit 111. Light-source control section 113 is composed of a publicly known computer, microcomputer and/or the like including an arithmetic unit, a controller, a storage, an input unit, an output unit, and/or the like, for example.

Response-light detection unit 130 detects fluorescence β generated by irradiation of the rear surface of metal film 30 with excitation light α during detection of a detection-target object, and plasmon scattering light γ generated by irradiation of the rear surface of metal film 30 with excitation light α during positioning of analysis chip 10 and during measurement of the enhanced angle. Response-light detection unit 130, for example, includes light reception unit 131, position-switching mechanism 132 and sensor control section 133.

Light reception unit 131 is disposed in the normal direction of metal film 30 of analysis chip 10 (the z-axis direction in FIG. 1). Light reception unit 131 includes first lens 134, optical filter 135, second lens 136, and light reception sensor 137.

First lens 134 is, for example, a condenser lens, and condenses the light emitted above from metal film 30. Second lens 136 is, for example, an image forming lens, and images the light condensed by first lens 134 on the light reception surface of light reception sensor 137. The light paths between the lenses are substantially parallel to each other. Optical filter 135 is disposed between the lenses.

Optical filter 135 guides only a fluorescent component to light reception sensor 137 and removes the excitation light component (plasmon scattering light γ) in order to detect fluorescence β with a high S/N ratio. Examples of optical filter 135 include an excitation light reflection filter, a short wavelength cut filter, and a bandpass filter. Optical filter 135 is, for example, a filter including a multilayer film that reflects a predetermined light component, but may be a color glass filter that absorbs a predetermined light component.

Light reception sensor 137 detects fluorescence β or plasmon scattering light γ. The sensitivity of light reception sensor 137 is so high that light reception sensor 137 can detect weak fluorescence β or plasmon scattering light γ from a slight amount of detection-target substance. Light reception sensor 137 is, for example, a photomultiplier tube (PMT), an avalanche photodiode (APD) or the like.

Position-switching mechanism 132 switches the position of optical filter 135 between a position on the light path and a position outside of the light path in light reception unit 131. More specifically, optical filter 135 is disposed on the light path of light reception unit 131 when light reception sensor 137 detects fluorescence β, and optical filter 135 is disposed outside the light path of light reception unit 131 when light reception sensor 137 detects plasmon scattering light γ. Position-switching mechanism 132 is composed of a turn driving section and a publicly known mechanism (such as a turntable and a rack-and-pinion) that moves optical filter 135 in a horizontal direction by utilizing turning movement, for example.

Sensor control section 133 controls detection of an output value of light reception sensor 137, management of the sensitivity of light reception sensor 137 according to the detected output value, change of the sensitivity of light reception sensor 137 for obtaining an appropriate output value, and the like. Sensor control section 133 is composed of a publicly known computer, microcomputer, and/or the like including an arithmetic unit, a controller, a storage, an input unit, and an output unit, for example.

Liquid-feeding unit 140 supplies a sample solution, labeling solution, washing solution and/or the like into channel 41 of analysis chip 10 held by chip holder 154. Liquid-feeding unit 140 includes chemical-liquid chip 141, syringe pump 142 and liquid-feeding pump driving mechanism 143.

Chemical-liquid chip 141 is a container for housing liquid such as a sample solution, labeling solution, and washing solution. Usually, as chemical-liquid chip 141, a plurality of containers are disposed in accordance with types of liquid, or a chip formed by integrating a plurality of containers is disposed.

Syringe pump 142 is composed of syringe 144 and plunger 145 capable of reciprocating in syringe 144. The reciprocation of plunger 145 quantitatively makes suction and discharge of liquid. When syringe 144 is replaceable, washing of syringe 144 is unnecessary. This configuration is favorable in terms of preventing entry of impurities. When syringe 144 is not replaceable, adding a configuration to wash the inside of syringe 144 makes it possible to use syringe 144 without replacement of syringe 144.

Liquid-feeding pump driving mechanism 143 includes a driving unit of plunger 145 and a moving unit of syringe pump 142. The driving unit of syringe pump 142 is a device for reciprocating plunger 145 and includes a stepping motor, for example. The driving unit including a stepping motor can manage the liquid feed amount and liquid feed speed of syringe pump 142, so that it is favorable in term of management of the amount of residual liquid of analysis chip 10. The moving unit of syringe pump 142, for example, freely moves syringe pump 142 in two directions including the axial direction (e.g., vertical direction) of syringe 144 and a direction crossing the axial direction (e.g., horizontal direction). The moving unit of syringe pump 142 is composed of a robot arm, a biaxial stage or a vertically movable turntable, for example.

Preferably, liquid-feeding unit 140 further includes a device that detects the position of a leading end of syringe 144 in terms of adjusting the relative heights of syringe 144 and analysis chip 10 to keep them constant, and managing the amount of residual liquid in analysis chip 10 to keep it constant.

Liquid-feeding unit 140 sucks various kinds of liquid from chemical-liquid chip 141 and supplies the liquid into channel 41 of analysis chip 10. At this time, moving plunger 145 causes the liquid to reciprocate in channel 41 in analysis chip 10 to agitate the liquid in channel 41. In this manner, uniformization of the density of liquid, acceleration of reaction (e.g., antigen-antibody reaction) in channel 41, and/or the like can be achieved. From the view point of performing the above-mentioned operations, analysis chip 10 and syringe 144 are preferably configured such that an inlet of analysis chip 10 is protected with a multilayer film and can be sealed when syringe 144 penetrates through the multilayer film.

The liquid in channel 41 is again sucked by syringe pump 142 and discharged to chemical-liquid chip 141 and/or the like. Repeating the above-mentioned operations carries out reaction, washing and the like using various kinds of liquid, thereby making it possible to dispose a detection-target substance labeled by a fluorescent substance in capturing region A in channel 41.

Conveyance unit 150 conveys analysis chip 10 to a measurement position or a liquid-feeding position and fixes analysis chip 10 thereto. The term "measurement position" herein refers to a position where excitation-light irradiation unit 110 irradiates analysis chip 10 with excitation light α, and response-light detection unit 130 detects fluorescence β or plasmon scattering light γ generated with the irradiation. In addition, the term "liquid-feeding position" herein refers to a position where liquid-feeding unit 140 supplies liquid into channel 41 of analysis chip 10 or removes the liquid in channel 41 of analysis chip 10. Conveyance unit 150 includes conveyance stage 152 and chip holder 154. Chip holder 154 is fixed to conveyance stage 152 so as to detachably hold analysis chip 10. Chip holder 154 has a shape capable of holding analysis chip 10 without blocking the light paths of excitation light α. For example, chip holder 154 is provided with an opening through which excitation light α passes. Conveyance stage 152 moves chip holder 154 in a certain direction (X-axis direction in FIG. 1) and a direction opposite to the certain direction. Conveyance stage 152 is driven by a stepping motor or the like, for example.

Control section 160 controls angle-adjustment mechanism 112, light-source control section 113, position-switching mechanism 132, sensor control section 133, liquid-feeding pump driving mechanism 143 and conveyance stage 152. In addition, control section 160 functions also as a position adjustment section that identifies the position of the end portion of capturing region A in analysis chip 10 held by chip holder 154 and moves chip holder 154 by conveyance stage 152 to move capturing region A of analysis chip 10 to an appropriate measurement position on the basis of a detection result of response-light detection unit 130. Control section 160 is composed of a publicly known computer, microcomputer, and/or the like including an arithmetic unit, a controller, a storage, an input unit, and an output unit, for example.

Figure 3:
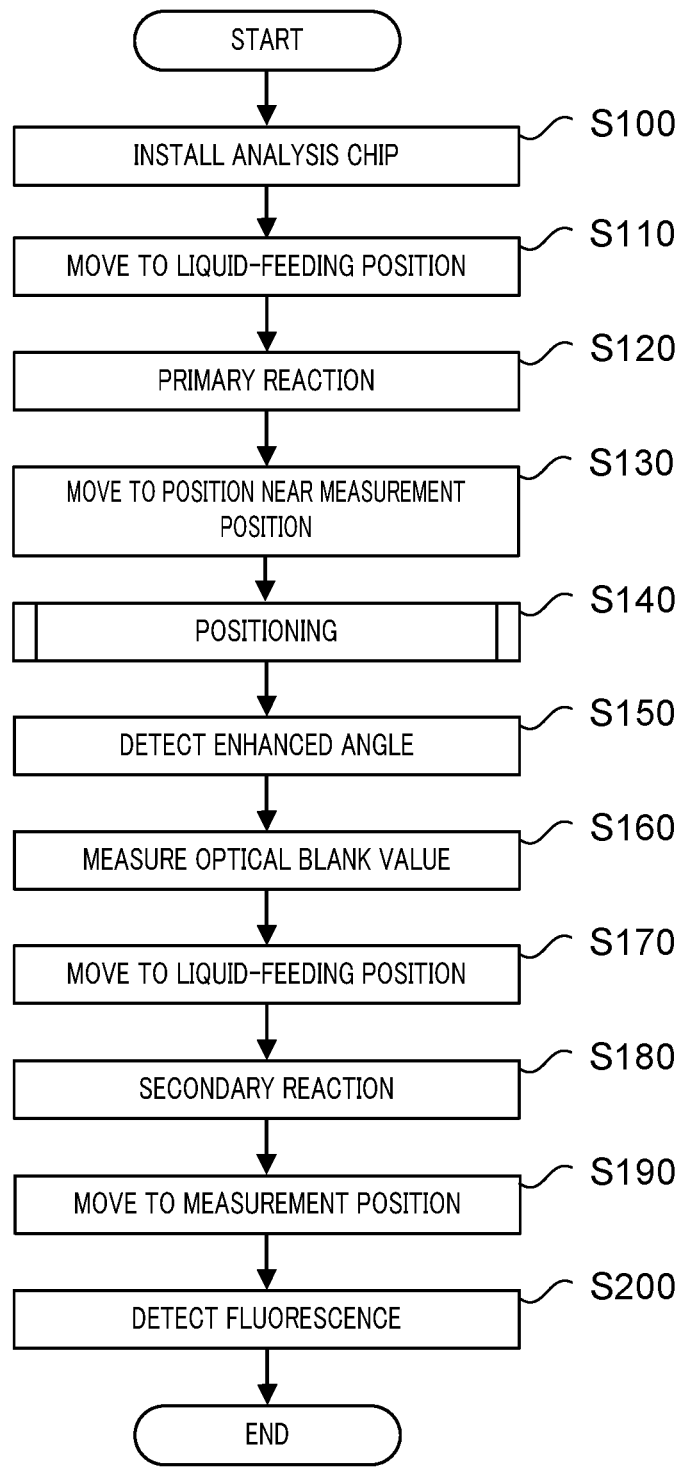
FIG. 3 is a flowchart illustrating an operation procedure of the SPFS device illustrated in FIG. 1.
Figure 4:
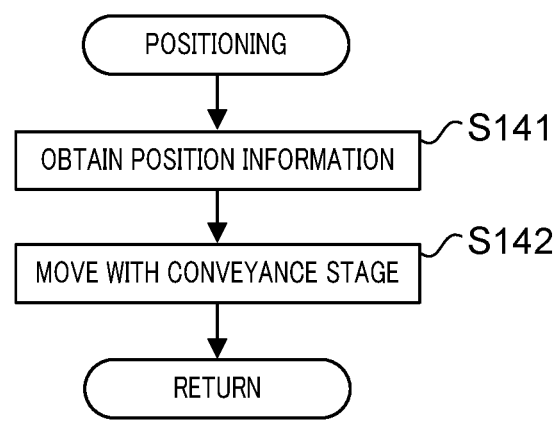
FIG. 4 is a flowchart illustrating steps in a positioning step (S140) illustrated in FIG. 3.

Next, a detection operation of SPFS device 100 (the surface-plasmon enhanced fluorescence measurement method according to Embodiment 1 of the present invention) will be described. FIG. 3 is a flowchart of an exemplary operation procedure of SPFS device 100. FIG. 4 is a flowchart illustrating steps in a position adjustment step (S140).

First, analysis chip 10 is installed in chip holder 154 of SPFS device 100 (S100). Next, control section 160 operates conveyance stage 152 to move analysis chip 10 to a liquid-feeding position (S110).

Subsequently, control section 160 operates liquid-feeding unit 140 to introduce the sample solution in chemical-liquid chip 141 into channel 41 of analysis chip 10 (S120). In channel 41, the detection-target substance is captured on metal film 30 by an antigen-antibody reaction (primary reaction). Thereafter, the sample solution in channel 41 is removed, and the interior of channel 41 is washed with a washing solution. Note that, when a moisturizing agent is present in channel 41 of analysis chip 10, the interior of channel 41 is washed prior to the introduction of the sample solution to remove the moisturizing agent in order for the capturing body to appropriately capture the detection-target substance.

Next, control section 160 operates conveyance stage 152 to move analysis chip 10 to a position near the measurement position (S130).

Figure 5:
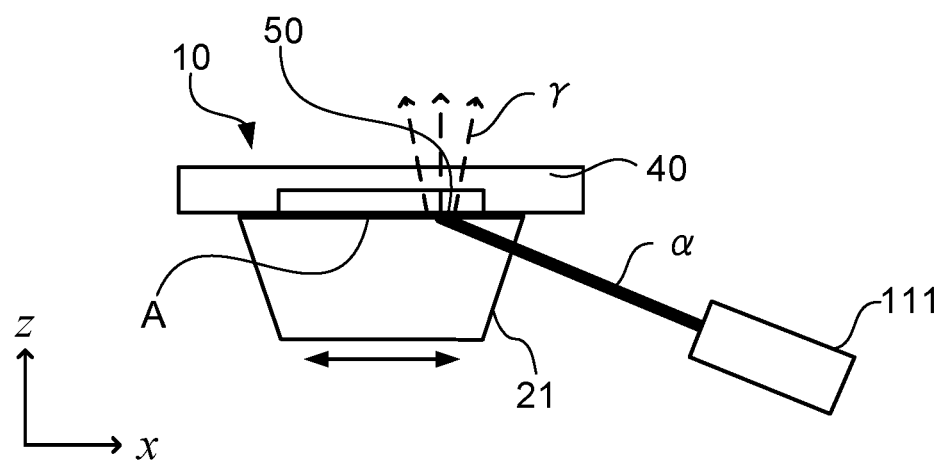
FIG. 5 is a schematic view for describing a step (S141) of obtaining position information on an end portion of the capturing region in an analysis chip.

Next, control section 160 operates excitation-light irradiation unit 110, response-light detection unit 130 and conveyance stage 152 to obtain the position information of the center of capturing region A and to adjust the position of capturing region A (analysis chip 10) on the basis of the obtained position information (S140). In this step, the region having a shape identical to mark 50 (region of the rear surface of metal film 30) and positioned right below mark 50 in analysis chip 10 held by chip holder 154 is irradiated with excitation light α, and plasmon scattering light γ emitted from mark 50 is detected to obtain the position information of the end portion of capturing region A of analysis chip 10 (S141). More specifically, scanning is performed on the irradiation spot on the rear surface of metal film 30 corresponding to mark 50 and the vicinity thereof to detect plasmon scattering light γ emitted from the vicinity of mark 50 and the other region (see FIG. 5). Scattered states (light amounts) of plasmon scattering light γ to be emitted from mark 50 and from the region in the vicinity of mark 50 are different. Thus, the position of mark 50 is identified from variation in the light amount of obtained plasmon scattering light γ. Next, the position of the center of capturing region A is identified from a distance between the center portion of previously set mark 50 and the position of the center portion of capturing region A. Accordingly, the degree of shifting in position of capturing region A from the measurement position can be identified. Next, chip holder 154 is moved by conveyance stage 152 to dispose capturing region A of analysis chip 10 at an appropriate measurement position on the basis of the obtained position information (S142).

Next, control section 160 operates excitation-light irradiation unit 110 and response-light detection section 130 to irradiate analysis chip 10 disposed at an appropriate position with excitation light α, and to detect plasmon scattering light γ having a wavelength identical to that of excitation light α to detect the enhanced angle (S150). More specifically, control section 160 operates excitation-light irradiation unit 110 to perform scanning of an incident angle of excitation light α with respect to metal film 30 and also operates response-light detection unit 130 to detect plasmon scattering light γ. At this time, controller 160 operates position-switching mechanism 132 to dispose optical filter 135 at a position outside of the light path of light reception unit 131. Control section 160 then determines the incident angle of excitation light α at which the light amount of plasmon scattering light γ is largest to be the enhanced angle.

Next, control section 160 operates excitation-light irradiation unit 110 and response-light detection section 130 to irradiate analysis chip 10 disposed at an appropriate measurement position with excitation light α and records an output value (optical blank value) of light reception sensor 137 (S160). At this time, control section 160 operates angle-adjustment mechanism 112 to set the incident angle of excitation light α to the enhanced angle. Furthermore, control section 160 controls position-switching mechanism 132 to dispose optical filter 135 inside the light path of light reception unit 131.

Next, control section 160 operates conveyance stage 152 to move analysis chip 10 to the liquid-feeding position (S170).

Subsequently, control section 160 operates liquid-feeding unit 140 to introduce liquid (labeling solution) containing a secondary antibody labeled by a fluorescent substance into channel 41 of analysis chip 10 (S180). In channel 41, through an antigen-antibody reaction (secondary reaction), a detection-target substance captured on metal film 30 is labeled by the fluorescent substance. Thereafter, the labeling solution in channel 41 is removed, and the interior of channel 41 is washed with a washing solution.

Next, control section 160 operates conveyance stage 152 to move analysis chip 10 to the appropriate measurement position determined in step S140 (S190).

Next, control section 160 operates excitation-light irradiation unit 110 and response-light detection unit 130 to irradiate analysis chip 10 disposed at the appropriate measurement position with excitation light α and to detect fluorescence β emitted from the fluorescent substance labeling the detection-target substance captured by the capturing body (S200). Control section 160 subtracts the optical blank value from the detection value to calculate the intensity of the fluorescence correlating with the amount of the detection-target substance. The intensity of the fluorescence thus detected is converted into the amount, density, and/or the like of the detection-target substance as appropriate.

Through the above-mentioned procedure, the presence or amount of the detection-target substance in the sample solution can be detected.

Note that, the detection of the enhanced angle (S150) may be performed before the primary reaction (S120). In this case, the determination of the measurement position of analysis chip 10 (S130 and S140) is also performed before the primary reaction (S110 and S120). Additionally, when the incident angle of excitation light α is determined in advance, detection of the enhanced angle (S150) may be omitted. In this case as well, the determination of the measurement position of analysis chip 10 (S130 and S140) is also performed before the measurement of an optical blank value (S160). As described above, the determination of the measurement position of analysis chip 10 (S130 and S140) is favorably performed before an optical measurement (detection of the enhanced angle, measurement of the optical blank value, or detection of the fluorescence) is performed for the first time.

In the above description, the step in which a detection-target substance and a capturing body are caused to react with each other (primary reaction, S120) is performed is followed by the step in which a detection-target substance is labeled by a fluorescent substance (secondary reaction, S180) (two-step scheme). However, the timing at which the detection-target substance is labeled by the fluorescent substance is not limited to any particular timing. For example, a labeling solution may be added to a sample solution to label the detection-target substance by the fluorescent substance in advance prior to introduction of the sample solution into channel 41 of analysis chip 10. Moreover, the sample solution and labeling solution may be injected into channel 41 of analysis chip 10 simultaneously. In the former case, injecting the sample solution into channel 41 of analysis chip 10 causes the capturing body to capture the detection-target substance labeled by the fluorescent substance. In the latter case, while the detection-target substance is labeled by the fluorescent substance, the detection-target substance is captured by the capturing body. In either case, the introduction of the sample solution into channel 41 of analysis chip 10 completes both the primary reaction and the secondary reaction (one-step scheme). When one-step scheme is adopted in the manner described above, detection of the enhanced angle (S150) is performed before antigen-antibody reaction, and determination of the measurement position of analysis chip 10 (S130 and S140) is performed even before the detection of the enhanced angle (S150).

Moreover, the timing at which positioning step (S140) is performed may not be before the primary reaction (S120) as long as it is performed before detection of the fluorescence emitted from the fluorescent substance obtained by labeling the detection-target substance with fluorescence. For example, positioning step (S140) may be performed before the primary reaction (S120) or after the primary reaction (S120) or after the primary reaction (S120) but before the secondary reaction (S180).

For SPFS device 100 described above, a description has been given of SPFS device 100 in which conveyance stage 152 moves only in the X direction in FIG. 1, but a configuration in which conveyance stage 152 also moves in the Y direction (direction perpendicular to the sheet surface) in FIG. 1 may be employed. In this configuration, the conveyance stage includes an X-direction moving mechanism to move chip holder 154 in the X direction and a Y-direction moving mechanism to move chip holder 154 in the Y direction. Furthermore, in an SPFS device including conveyance stage 152 movable in a planar direction, scanning of an irradiation spot can be performed in multiple directions, so that the detection accuracy for the end portion of capturing region A can be further improved. The Y-direction moving mechanism may include a driving mechanism configured to drive excitation-light irradiation unit 110, or to drive excitation-light irradiation unit 110 and response-light detection unit 130 integrally. Note that, two marks 50 may be disposed in this case.

INDUSTRIAL APPLICABILITY

The surface-plasmon enhanced fluorescence measurement method and the surface-plasmon enhanced fluorescence measurement device, and the analysis chip according to the present invention enable detection of a detection-target substance with high reliability, and therefore are suitable for laboratory tests and/or the like, for example.

REFERENCE SIGNS LIST

10 Analysis chip
20 Prism
21 Incidence surface
22 Film-formation surface
23 Emission surface
30 Metal film
40 Channel closure
41 Channel
50 Mark
100 SPFS device
110 Excitation-light irradiation unit
111 Light source unit
112 Angle-adjustment mechanism
113 Light-source control section
130 Response-light detection unit
131 Light reception unit
132 Position-switching mechanism
133 Sensor control section
134 First lens
135 Optical filter
136 Second lens
137 Light reception sensor
140 Liquid-feeding unit
141 Chemical-liquid chip
142 Syringe pump
143 Liquid-feeding pump driving mechanism
144 Syringe
145 Plunger
150 Conveyance unit
152 Conveyance stage
154 Chip holder
160 Control section
α Excitation light
β Fluorescence
γ Plasmon scattering light

The invention claimed is:

1. A position-detection method on a surface-plasmon field-enhanced fluorescence spectroscopy device, the method comprising:
   (a) disposing, in a position configured to receive an excitation light, an analysis chip having a metal film surface, the metal film surface including:
      (i) an incident side for receiving the excitation light;
      (ii) an emission side for emitting scattered plasmon lights when the incident side is irradiated with the excitation light;
      (iii) a capturing region including a fixed capturing body capturing a detection-target substance; and
      (iv) a positioning mark that, when irradiated with the excitation light, emits a first scattered plasmon light in a first state, wherein the first scattered plasmon light is different from a second plasmon light in a second state emitted by the metal film surface that does not include the positioning mark;
   (b) scanning the excitation light across a portion of the metal film surface, wherein the scanned portion of the metal film surface includes the positioning mark and a portion of the area outside of the positioning mark;
   (c) detecting the first scattered plasmon light in the first state;
   (d) determining a position of the positioning mark based on the detection of the first scattered plasmon light in the first state; and
   (e) determining a position of the capturing region according to the position of the positioning mark.

2. The position-detection method according to claim 1, the method further comprising:
   setting the position of the capturing region as an irradiation position to which the excitation light is to be irradiated.

3. The position-detection method according to claim 1, wherein the positioning mark is a seal attached to the metal film surface.

4. The position-detection method according to claim 1, wherein the metal film is formed on a film-formation surface of a prism included in a analysis chip.

5. The position-detection method according to claim 4, wherein the positioning mark is a protrusion or a recess formed on the film-formation surface, or an exposed portion of the film-formation surface that is not covered by the metal film.

6. The position-detection method according to claim 1, wherein the positioning mark is formed on the same surface as the metal film.

7. The position-detection method according to claim 6, wherein the positioning mark is a patterned region of the metal film.

8. The position-detection method according to claim 1, wherein the positioning mark is formed in a position different from the capturing region.

9. The position-detection method according to claim 1, wherein there is only one positioning mark.

10. The position-detection method according to claim 1, wherein the positioning mark has a size no bigger than the capturing region.

11. The position-detection method according to claim 1, wherein the position of the capturing region is determined according to the position of the positioning mark and a predetermined positional relation of the capturing region with respect to the positioning mark.

12. The position-detection method according to claim 2, wherein the irradiation position is set by moving the analysis chip so that the excitation light irradiates the position of the capturing region.

13. An apparatus for detecting a position on a chip used in surface-plasmon field-enhanced fluorescence spectroscopy comprising:
a light source that irradiates a capturing region of an analysis chip with an excitation light, the capturing region including a fixed capturing body for capturing a detection-target substance; and
a detector coupled to a processor;
wherein the processor executes functions comprising:
scanning the excitation light on a metal film surface of the analysis chip that includes at least one positioning mark and the capturing region such that the capturing region and at least one positioning mark are irradiated;
analyzing scattered plasmon lights emitted from the metal film surface and detected by the detector, wherein the metal film surface includes the capturing region and the positioning mark and wherein the positioning mark emits a first scattered plasmon light with a first state different from a second state of a second scattered plasmon light emitted by the area outside the positioning mark upon irradiation by the excitation light;
indentifying the first scattered plasmon light with a first state;
determining a position of the positioning mark based on the identification of the first scattered plasmon light with the first state;
determining a position of the capturing region according to the position of the positioning mark; and
setting the position of the capturing region as the irradiation position to which the excitation light is to be irradiated.

14. The apparatus for detecting a position on a chip used in surface plasmon field-enhanced fluorescence spectroscopy according to claim 13 further comprising:
a conveyor which conveys the analysis chip, the analysis chip including a prism,
wherein the metal film is formed on a film-formation surface of the prism, and
wherein the processor further executes a function which controls the conveyor to move the analysis chip so that the excitation light is irradiated to the position of the capturing region.

15. An analysis chip for detecting a position on a chip used with surface plasmon field-enhanced fluorescence spectroscopy comprising:
a prism which includes a film-formation surface; and
a metal film formed on the film-formation surface of the prism, the metal film including a capturing region and at least one positioning mark, the capturing region including a fixed capturing body for capturing a detection-target substance;
wherein, when the positioning mark is irradiated with an excitation light, the positioning mark emits a first scattered plasmon light with a first state different from a second state of a second scattered plasmon light emitted by an area on the metal film outside the positioning mark when the area on the metal film outside the positioning mark is irradiated by the excitation light.

16. The analysis chip for detecting a position on a chip used with surface plasmon field-enhanced fluorescence spectroscopy according to claim 15, wherein the at least one positioning mark is at least one of:
a seal attached to the metal film surface;
a protrusion formed on the film-formation surface;
a recess formed on the film-formation surface;
an exposed portion of the film-formation surface that is not covered by the metal film; or
a patterned region of the metal film.

17. The analysis chip for detecting a position on a chip used with surface plasmon field-enhanced fluorescence spectroscopy according to claim 15,
wherein the at least one positioning mark is formed in a position different from the capturing region.

* * * * *